United States Patent [19]

Buffet

[11] 4,313,441
[45] Feb. 2, 1982

[54] METHOD OF ADJUSTING AN IMPLANTABLE CARDIAC STIMULATOR, AND ADJUSTMENT PROGRAMMER AND STIMULATOR FOR CARRYING OUT SAME

[75] Inventor: Jacques Buffet, Le Raincy, France

[73] Assignee: Cardiofrance - Compagnie Francaise d'Electrocardiologie, France

[21] Appl. No.: 30,816

[22] Filed: Apr. 17, 1979

[30] Foreign Application Priority Data

May 5, 1978 [FR] France .............................. 78 13332

[51] Int. Cl.³ .............................................. A61N 1/36
[52] U.S. Cl. ............................................ 128/419 PG
[58] Field of Search ................... 128/419 PG, 419 PS, 128/419 PT

[56] References Cited

U.S. PATENT DOCUMENTS

| | | | |
|---|---|---|---|
| 3,677,251 | 7/1972 | Bowers | 128/419 PG |
| 4,124,031 | 11/1978 | Mensink et al. | 128/419 PG |
| 4,126,139 | 11/1978 | Walters et al. | 128/419 PG |
| 4,166,470 | 9/1979 | Neumann | 128/419 PG |

OTHER PUBLICATIONS

Heethaar et al., "Medical & Biological Engineering", vol. 15, #2, Mar. 1977, pp. 90–97.

Primary Examiner—William E. Kamm
Attorney, Agent, or Firm—Robert E. Burns; Emmanuel J. Lobato; Bruce L. Adams

[57] ABSTRACT

A process of regulating by an extra-corporeal control unit an implanted cardiac stimulator comprising a pulse generator and a pair of electrodes, comprises controlling the stimulator so that it functions at a fixed rhythm independent of normal cardiac rhythm and detecting by the extra-corporeal unit successive pulses emitted by the stimulator. After each of selected stimulator pulses detected, and during the whole period between successive stimulator pulses, a train of successive control pulses is transmitted by the control unit and is received by the stimulator as binary information "1". On the contrary, no train of successive control pulses is transmitted during the whole period between other successive stimulator pulses and this is received as binary information "0". The binary information thus received is used to regulate the operation of the stimulator. The extra-corporeal unit displays the pulses emitted by the stimulator to verify that the regulator is effective.

8 Claims, 5 Drawing Figures

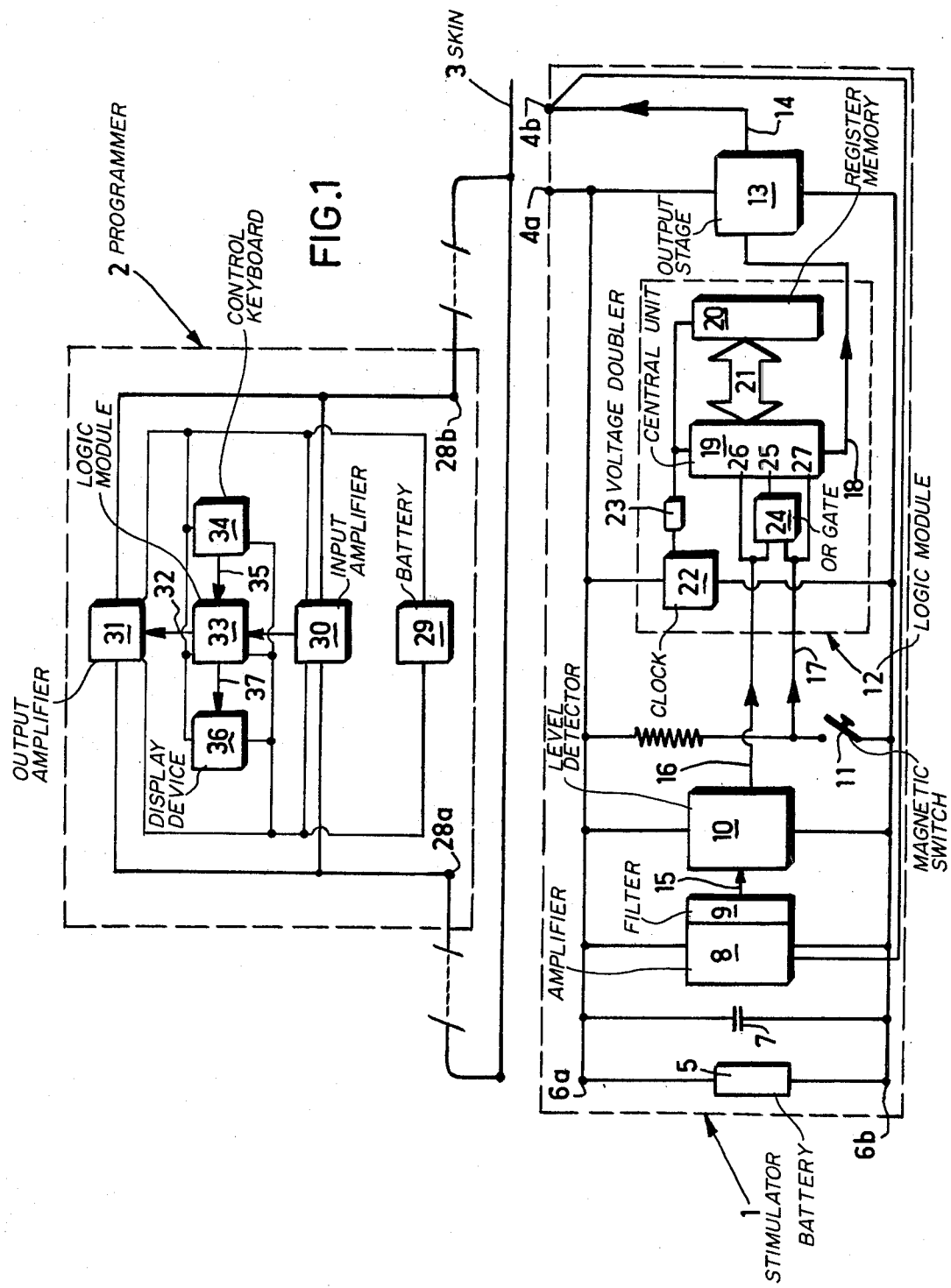

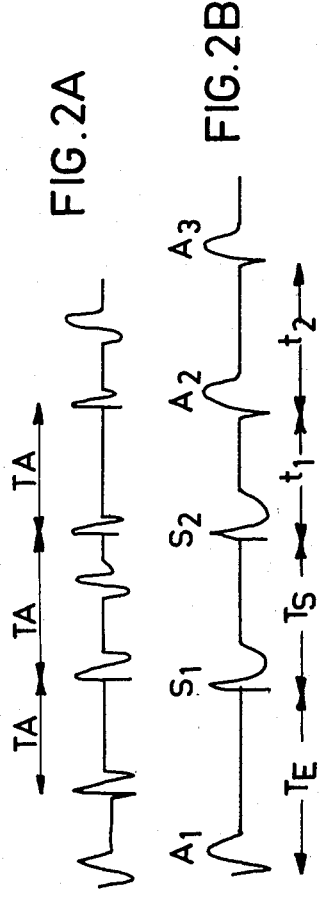
FIG. 2A
FIG. 2B
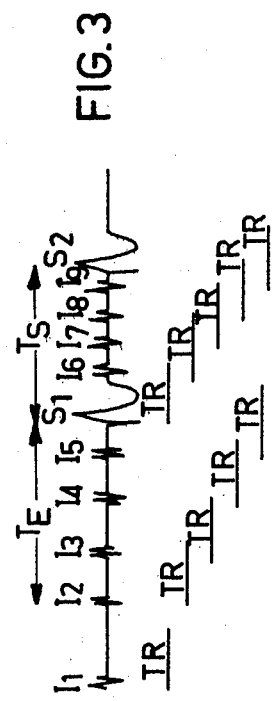
FIG. 3
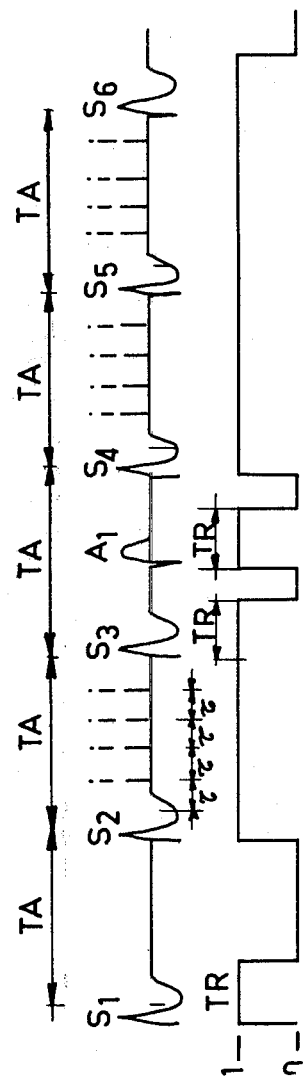
FIG. 4

METHOD OF ADJUSTING AN IMPLANTABLE CARDIAC STIMULATOR, AND ADJUSTMENT PROGRAMMER AND STIMULATOR FOR CARRYING OUT SAME

BACKGROUND OF THE INVENTION

1. Field of the Invention

This invention relates to a method of adjusting an implantable cardiac stimulator or pacemaker from outside the patient's body; a programmer, on the one hand and a cardiac stimulator, on the other hand, for carrying out the method; and the functionally unitary assembly comprising the stimulator and the programmer.

2. Description of the Prior Art

Methods of adjusting an implantable and adjustable cardiac stimulator through means located outside the patient's body are already known in the art. This heart stimulator comprises a probe electrically connected to a case containing: a source of electric current; an amplifier and a filter; a logic module of which the function consists in generating stimulating pulses; an output stage capable of feeding calibrated pulses to the probe; and, finally, a flexible-blade switch normally urged to its open-circuit position and adapted to be short-circuited when exposed to a magnetic field, notably of extra-corporeal origin. The function of the magnetic switch is to control the programme of operation of the logic module, notably a general programme in which the cardiac stimulator operates as a "demand" unit, and a particular programme.

In the first known method of adjusting the implantable cardiac stimulator a permanent magnet is brought close to the site where the stimulator is inserted, so as to short-circuit the magnetic switch and thus start a particular logic programme describing sequentially the various conditions of the adjustable characteristic to be programmed. When the desired specific value is attained, the magnet is removed so that the magnetic switch will resume its open position and the cardiac stimulator operates normally according to the demand with the characteristic at the programmed value. This method is advantageous in that the apparatus required outside the patient's body is particularly small (permanent magnet). However, it is objectionable in that it is difficult to carry out since the magnet must be removed quickly at the proper time. Moreover, with this method only one and single characteristic of the stimulator can be adjusted.

In a second known method an electromagnet located outside the patient's body is used close to the location where the cardiac stimulator or pacemaker is inserted. The electromagnet coil is controlled in such particular way that a pulsating magnetic field is created, in order to open and close the magnetic switch according to a particular mode corresponding to a coded information processed by the logic module determining which is the characteristic to be adjusted on the one hand and the adjustment value of this value on the other hand. It can be said to the credit of this method that is permits a polyvalent adjustment. However, the degree of safety is far from perfect since on the one hand only one control action is performed and on the other hand the programmer cannot control the accuracy with which the data are taken into account by the stimulator.

In a third known method a high-frequency electromagnetic emission modulated both in frequency and amplitude is transmitted through extra-corporeal means. This emission is collected by an implanted antenna so as to be detectable. With this method it is also possible to cause the variation of several adjustable characteristics of a stimulator. However, with this third method the stimulator must be modified since it requires the incorporation of means for receiving the electromagnetic emission.

From the foregoing it is clear that these known methods are either limited as to their field of application, or difficult or awkward to use, or rather unreliable, or require a specific transformation or conversion of the cardiac stimulator or pacemaker.

SUMMARY OF THE INVENTION

It is the essential object of this invention to avoid the above-mentioned inconveniences. To this end, it provides a method of adjusting an implantable cardiac stimulator adjustable through extra-corporeal means, this method consisting in controlling the stimulator from outside the patient's body so that it will operate at a fixed frequency independent of the spontaneous or self-sustained heartbeat; detecting, also through means lying outside the patient's body, the successive pulses emitted by the stimulator; and controlling through extra-corporeal means from each detected pulse and during the complete stimulation period the emission or, on the contrary, the non-emission of a signal corresponding to binary (1 or 0) information received and detected as such by the stimulator.

According to other features characterizing this invention, the emitted signal corresponds to a train of waves having a period lower than the refractory period of the stimulator.

It is another object of this invention to provide implantable cardiac stimulator adjustable through extra-corporeal means and provided with a programmer; a programmer adapted to operate with a cardiac stimulator, and, finally, the functional assembly comprising the cardiac stimulator and the programmer.

Other features and advantages of the invention will appear as the following description proceeds with reference to the attached drawings.

BRIEF DESCRIPTION OF THE DRAWINGS

FIG. 1 is a block diagram illustrating the functional assembly comprising the graftable cardiac stimulator and the extra-corporeal programmer;

FIGS. 2A and 2B are diagrams illustrating the mode of operation of the cardiac stimulator with the relay closed and open, respectively;

FIG. 3 is a diagram illstrating the refractory period of the stimulator, and

FIG. 4 is a diagram illustrating the mode of operation of the programmer-stimulator assembly according to this invention.

DESCRIPTION OF THE PREFERRED EMBODIMENT

In the method of the present invention, an implantable, multi-adjustment cardiac stimulator or pacemaker is adapted to be adjusted through extra-corporeal means by controlling same from outside the patient's body in such a way that it operates at a fixed frequency independent of the patient's spontaneous heartbeat; the successive pulses emitted by the stimulator are detected also through extra-corporeal means; by using likewise extra-corporeal means, and from each detected pulse and during the complete stimulation period, the emission or on the contrary the non-emission of a signal corresponding to binary information "1" or "0" received and detected as such by the stimulator is controlled. In a specific form of embodiment given by way of example, not of limitation, the emitted signal consists of a train of pulses having a period lower than the refractory period of the stimulator.

According to this invention, there is provided a functional assembly comprising in combination an implantable, multi-adjustment cardiac stimulator 1 and an extra-corporeal programmer 2 disposed close to the patient's skin 3 in the insertion area of the implanted stimulator 1.

The stimulator 1 is of the type known as a "sentry" stimulator adapted to be associated with a cardiac probe (not shown) and comprising a case with a pair of electrodes 4a, 4b, connected with the probe of the stimulator and, in this case, a self-contained source 5 of electric current, for example a storage battery, provided with lead wires 6a and 6b of which one, for instance 6a, is connected to the electrode 4a. Connected in parallel across the lead wires 6a and 6b are the following component elements: a capacitor 7, an amplifier 8 with its filter 9; a level detector 10, a magnetically operable switch 11; a logic module designated in general by the reference numeral 12, and an output stage 13 connected via a wire 14 to the electrode 4b. Other connecting wires 15, 16, 17 and 18 connect the amplifier 8 and its filter 9 to the level detector 10; this level detector 10 is connected to the logic module 12, and the magnetic switch 11 is also connected to the logic module 12 and the latter to the output stage 13.

The function of amplifier 8 and of its filter 9 is to amplify and filter the signals detected on electrodes 4a and 4b. The coefficient of voltage amplification is notably of the order of 500. The filter 9 is notably of the band-pass type centered to a frequency equal or substantially equal to 60 Hertz.

The level detector 10 is switched off when the output level of amplifier 8 and filter 9 exceeds a predetermined value, for example of the order of about 0.5 Volt. As a result, any signal detected on the electrodes and tuned to the band pass and having an amplified amplitude beyond the switching threshold of detector 10 will cause this detector 10 to switch off.

The function of the logic module 12 is to generate stimulation pulses in synchronism with the output signals of level detector 10. This logic module comprises a central processing unit 19, a register memory 20 connected via a bus circuit 21 to said central processing unit 19; a clock 22 connected to lead lines 6a and 6b, a voltage doubling circuit 23 disposed between the clock 22 and the central processing unit 19 on the one hand and the memory 20 on the other hand; a logic OR gate 24 connected to the input 25 of central processing unit 19 and to the connecting wires 16 and 17. The OR gate 24 is also connected to the two "Display" inputs 26, 27 of central unit 19 to which lead 18 is connected. The central processing unit 19 will thus produce a programme of which the data are stored in hexadecimal language in memory 20 via bus circuit 21. This programme is delivered under under the control of pulses from clock 22. Preferably, microprocessors are used in this central unit.

The function of output stage 13 is to feed calibrated pulses shaped in accordance with the output signals of logic module 12 to the electrodes 4a, 4b.

The magnetic switch 11 consists notably of a flexible-blade switch normally urged to its open-circuit position but adapted to be tilted to its closed-circuit position by detachable, extra-corporeal means, notably magnetic means and, more particularly, a member generating a magnetic field, for example a permanent magnet.

The extra-corporeal and detachable programmer 2 is adapted to be associated with electrodes (not shown), connected across terminals 28a, 28b. It comprises a case (not shown) enclosing an input amplifier 30 and an output amplifier 31 connected in parallel across said terminals 28a and 28b. and a self-contained source of electric current 29, such as a storage battery supplying power for the amplifiers. The input amplifier 30 is connected to the output amplifier 31 via a connection 32 in which a logic module 33 is interposed. A control keyboard 34 is connected to this logic module 33 via a connection 35 and the module 33 is connected via another connection 37 to an alphadigital display device 36.

Furthermore, the function of the input amplifier 30 provided with a filter is to collect the signals received via terminals 28a, 28b from the electrodes. The passband of this amplifier is such that only signals corresponding to a pulse emitted by stimulator 1 are collected.

The logic module 33 is intended for generating control pulses in response to the input amplifier 30 according to the specific instructions given through the medium of the keyboard 34 and displayed on the digital display device 36. It is thus possible to programme manually by means of keyboard 34 the desired adjustment of the variable of stimulator 1.

The purpose of output amplifier 31 is to deliver pulses calibrated and shaped according to the output signals of logic module 33 to terminals 28a, 28b.

OPERATION

When the magnetic switch 11 is short-circuited as a consequence of the presence of an external magnetic field, and considering the connection between the switch and the "Break" input 25 of central processing unit 19, a specific programme is started without which the stimulator emits pulses at a constant period TA, independently of any natural or spontaneous heartbeat and independent of the normal stimulation period TS. The variation of period TA in time denotes the degree of exhaustion of the source 5 of electric current (the period increases when the source begins to fail). This mode of operation is illustrated in FIG. 2A. In this specific programme, the output of level detector 10, connected via connection 16 to the "Display" input 26, is regularly scanned. As a result, the logic module 12 is now capable of determining whether, during said period TA and between two successive pulses, signals such as successive interference trains exist or not.

FIG. 2B illustrates the mode of operation of stimulator 1 when the magnetic switch 11 is open, that is, not responsive to an extra-corporeal magnetic field. In this case, the stimulator 1 performs its normal therapeutical stimulating function.

FIG. 2B illustrates a particular case. A spontaneous or natural cardiac wave is shown at A1. If no self-sustained or spontaneous cardiac activity follows this wave A1, the stimulator, at the end of a so-called "exhaust" period TE, emits a stimulation pulse S1. If no self-sustained wave is detected after the stimulation pulse S1, the stimulator 1 emits at the end of period TS a stimulation pulse S2. A self-sustained wave A2 appearing after the stimulation pulse S2, at the end of a time lapse t1 shorter than TS, the stimulator 1 is recycled and thus not required to deliver a stimulation pulse. If, after the self-sustained wave A2, another self-sustained wave A3 appears after a time t2 shorter than TE, the stimulator is likewise recycled.

Superposed to these general modalities are other specific modalities resulting from the refractory period TR which is the time period elapsing while the detected signals are not voluntarily taken into account. The refractory period is such that the electromagnetic interferences having a recurrency period lower than the refractory period TR cannot recycle the stimulator. Suppose for example the signal I1 which is an electrical interference of any origin, detected by the stimulator. This signal is not distinguished from a cardiac wave by the stimulator and will thus cause the stimulator to be recycled during a period equal to the exhaust period TE. As a consequence of signal I1, the stimulator 1 will comply with the refractory period TR. If the signal I2 occurs after a timer period longer than TR but shorter than TE, it causes the stimulator 1 to be recycled during the exhaust period TE. The signal I3 occurs after a time lapse shorter than TR. Consequently, the stimulator is not recycled but the refractory period is renewed from I3 on. Similarly, if the signal I4 occurs during the refractory period following I3, the effect described with reference to I3 is reproduced from I4 on. The same applies to signal I5. After the exhaust period TE following the signal I2, a stimulation pulse S1 occurs. The latter starts another refractory period TR. The signal I6, during this refractory period, causes likewise no recycling and, as explained in the foregoing, the renewal of this period; the same applies to signals I7, I8 and I9. After a stimulation period TS commencing with the stimulation pulse S1, the stimulator 1 emits a stimulation pulse S2.

The programmer 2 operates in combination or in conjunction with the stimulator in order to permit the adjustment of a variable thereof. In this case, a stimulation pulse emitted by the cardiac stimulator or pacemaker 1 is detected by the electrodes associated with the programmer 2 and acknowledged as such by the input amplifier 30. The data concerning on the one hand a variable to be adjusted, and on the other hand a value to be imparted to this variable, are fed to the logic module 33 via the keyboard 34, so that to each pulse transmitted from the input amplifier 30 to the logic module 33 there corresponds a signal, or an absence of signal, during the time elapsing between two successive pulses. This signal, or this absence of signal, is fed to the output amplifier 31 which applies it to the electrodes associated with the programmer so as to be subsequently acknowledged as such by the inserted or grafted cardiac stimulator 1.

In practice, the programming or adjustment is permitted when the magnetic switch 11 is short-circuited and the stimulator 1 emits pulses at period TA. Since, as will be explained presently, the programmer can possibly operate when the stimulator operates according to the general programme, it is preferred that the permanent magnet creating the magnetic field for short-circuiting the magnetic switch 11 be materially distinguished or separated from the programmer. However, it is clear that this permanent magnet may constitute a unitary assembly with the programmer proper.

The electrodes associated with the programmer are disposed in a known fashion whereby electrocardiograms can be recorded. More particularly, the electrodes are kept in contact with the patient's skin at two points adequately spaced from each other, for example the right arm and the left arm. The input amplifier 30 distinguishes among the input signals the stimulating pulses from the self-sustained or spontaneous waves and from the other signals by virtue of the pass band calculated for this purpose.

According to an important feature characterizing this invention, the output signal emitted by output amplifier 31 is a train of N pulses having a period lower than the refractory period. As a result, according to the presence or the absence of any signal from output amplifier 31, i.e. the presence or the absence of the train of N pulses, the refractory period of stimulator 1 is renewed or not throughout its period TA elapsing between two successive pulses. With magnetic switch 11 thus short-circuited, the output of level detector 10, where the presence or the absence of the train of pulses is scanned by the logic module 12 which reduces, as a "1" or "0" information, the renewal or non-renewal of the refractory period between two successive pulses.

To this end, from the very first transmission of information "1", the logic module 12 will assume the programming mode and thus be able to record the successive information constituting a binary word to which a particular adjustment or setting of the stimulator corresponds.

FIG. 4 illustrates by way of example the transmission of the binary word "1011". S1 is a stimulation pulse. From S1 on, and during the time TR, the refractory period elapses and ceases when a stimulation pulse S2 is emitted at a time TA following S1. The transmission begins after S2. The programmer delivers in response to the stimulation pulse S2 a four-pulse train covering the period TA between stimulation pulse S2 and stimulation pulse S3. Consequently, and considering the period $\tau$ of these pulses i, the refractory period is extended during a time TR. Since, from the stimulation pulse S3 on, the programmer does not emit any train of pulses, the refractory period is not renewed and drops back to level 0. If a self-sustained or spontaneous wave A1 occurs in the period TA from and after pulse S3, the stimulator will resume for TR its refractory period which subsequently ceases until the stimulation pulse S4 is emitted after a time TA following the stimulation pulse S3. It is thus clear that, between the two stimulation pulses S3 and S4, no continuous and complete renewal of the refractory period took place. It will be seen that the different periods TA and TR respectively are such that even the generation of a spontaneous wave will not leave any doubt as to the discontinuity of the renewal of the refractory period.

From the stimulation pulse S4 on, the programmer emits a train of N pulses, until a stimulation S5 is emitted after a duration TA. The refractory period is thus renewed continuously between S4 and S5, and likewise between S5 and S6.

Of course, the data transmission code may be modified in many ways. However a three-part binary word may be taken as an example. The first part is a programming key, the second is the denomination of the parameter to be programmed among the various programmable parameters, and the third is the new value given to the parameter.

Should the case arise, the existence of control means for avoiding programmation errors may be contemplated.

It is obvious that the programming possibilities are extremely diversified. Therefore, it is not possible to give an exhaustive list thereof. However, by way of example, the following characteristics may be programmed if desired:

Stimulation period comprising sixteen stages between 500 and 1,300 milliseconds;

Width of the stimulation pulse in sixteen stages from 0.1 to 1.6 milliseconds;

Amplitude of the stimulation pulse in three stages of 2.5, 5 and 7.5 Volts;

Sensitivity of the stimulator amplifier in four stages of 0.5, 1.5, 4 and 10 millivolts;

Refractory period in eight stages from 50 to 450 milliseconds;

Exhaust period in sixteen stages from 500 to 1,300 milliseconds.

Each characteristic will thus correspond to a binary value (a word of four binary digits) stored in a data register of the central unit and utilized by the general programme.

In addition to a control data emitting function, the programmer is capable performing a data receiving function in connection with the stimulator operation. In this case, the programmer operates with or without the short-circuited magnetic switch 11, i.e. with or without magnetic field, according to requirements. As a result, the following data can be received on the display device 36:

Stimulation rhythm of the stimulator, so that the degree of exhaustion of the power cource 5 can be checked or ascertained;

Measuring the width of the stimulation pulse emitted by the stimulator; and

Measuring the amplitude of the stimulation pulse emitted by the stimulator.

Finally, the programmer is capable of emitting a pulse synchronized with a variable delay or time-lag, and adjustable in relation to the stimulating pulse of the stimulator for the various applications contemplated.

Of course, many modifications and changes may be brought to the practical embodiment of the component elements of the stimulator and of the programmer, without departing from the basic principles of the invention as set forth in the appended claims. What is claimed as new is:

1. Process of regulating by extra-corporeal means an implanted cardiac stimulator comprising means for generating pulses for stimulating the heart of a patient and a pair of electrodes by which said stimulative pulses are transmitted to the heart of the patient, said stimulator having a refractory period between successive pulses, said process comprising:

controlling the stimulator to generated pulses at a fixed frequency independent of the normal cardiac rhythm, detecting by said extra-corpeal means successive pulses emitted by the stimulator, transmitting after each of selected stimulator pulses detected during the whole period between successive stimulator pulses a train of successive control pulses which is received and detected by the stimulator as binary information "1" and, on the contrary, transmitting no train of successive control pulses during the whole period between other successive stimulator pulses as binary information "0", applying the binary information thus transmitted to the stimulator to regulate the operation of the stimulator, and thereupon displaying by said extra-corpeal means the pulses emitted by the stimulator to verify that the regulator is effective.

2. Process according to claim 1, in which the binary information "1" received and sensed by the stimulator corresponds to a continuous renewal of the refractory period of the stimulator between two successive stimulator pulses, and the binary information "0" corresponds to discontinuity or absence of the refractory period.

3. Process according to claim 1 or 2, in which the period between successive pulses of said train of control pulses is less than the refractory period of the stimulator.

4. Process according to claim 1, which of said stimulator is effected by a binary word of at least four binary digits.

5. Cardiac stimulating apparatus comprising:

an implantable cardiac stimulator comprising means for generating pulses for stimulating the heart of a patient, a pair of internal electrodes by which said stimulating pulses are transmitted to the heart of the patient, and means for receiving and sensing external control pulses, and extra-corporeal programming means comprising external electrodes for contacting the skin of the patient at spaced points to transmit and receive pulses, means for receiving through said external electrodes and displaying pulses transmitted by said stimulator, and means for transmitting through said external electrodes to said stimulator after each of selected stimulator pulses during the whole period between successive stimulator pulses a train of successive control pulses which are received and detected by the stimulator as binary information "1", no train of control pulses being transmitted during the whole period between other successive stimulator pulses, such absence of a train of control pulses being detected by said stimulator as binary information "0", said stimulator including means for regulating the operation of said stimulator in accordance with said binary information received from said programming means, and pulses thereafter emitted by said stimulator being received and displayed by said display means to verify that the regulation is effective.

6. Apparatus according to claim 5, in which the period between successive pulses of said train of control pulses is less than the refractory period of the stimulator.

7. Apparatus according to claim 5, in which said programming means comprises an energy source, an input amplifier and output amplifier connected with said energy source, means including a logic module connecting the output of said input amplifier with the input of said output amplifier, means connecting the input of said input amplifier and the output of said output amplifier with said external electrodes, a control keyboard connected with said logic module and means connecting said logic module with said display means.

8. Apparatus according to claim 5, in which said stimulator comprises a source of energy, an amplifier connected with said source of energy and with said internal electrodes, a filter of the output of said amplifier, level detector means connected through said filter to said amplifier, a logic module including memory means connected with said level detector, an output stage connecting said logic module with said internal electrodes and magnetically operable switch means connected with an imput of said logic module and operable to activate said logic module to scan the output of said level detector when said switch means is closed said switch means being operable by magnetic force applied externally.

* * * * *